(12) United States Patent
Dabora et al.

(10) Patent No.: US 7,229,614 B2
(45) Date of Patent: Jun. 12, 2007

(54) INTERFERON GAMMA IN THE DETECTION AND TREATMENT OF ANGIOMYOLIPOMAS

(75) Inventors: Sandra L. Dabora, Brookline, MA (US); David J. Kwiatkowski, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 581 days.

(21) Appl. No.: 10/609,680

(22) Filed: Jul. 1, 2003

(65) Prior Publication Data

US 2005/0112094 A1 May 26, 2005

Related U.S. Application Data

(60) Provisional application No. 60/393,102, filed on Jul. 3, 2002.

(51) Int. Cl.
*A61K 38/21* (2006.01)
*A61K 45/00* (2006.01)

(52) U.S. Cl. .................................. 424/85.5; 514/889

(58) Field of Classification Search ............... None
See application file for complete search history.

(56) References Cited

U.S. PATENT DOCUMENTS

| 4,666,865 A | 5/1987 | Chang et al. ............... 436/518 |
| 4,727,138 A | 2/1988 | Goeddel et al. ............ 536/27 |
| 6,218,132 B1 | 4/2001 | Spack et al. ............... 435/7.24 |
| 6,326,483 B1 | 12/2001 | Kwiatkowski et al. ...... 536/23.5 |

OTHER PUBLICATIONS

Ellerhorst et al. Phase II trial of low dose gamma-interferon in metastatic renal cell carcinoma (1994), J. of Urology, vol. 152, pp. 841-845*
ACTIMMUNE science insert.*
Anderson, et al., "Epithelioid Angiomyolipoma of the Ovary: A Case Report and Literature Review," *Intl. J. Gyn. Path*, 21:69-73.
Argenyi, et al., "Cutaneous Angiomyolipoma—A Light-Microscopic, Immunohistochemical, and Electron-Microscopic Study," *Am. J. Dermatopathol.* 13:497-502 (1991).
Bernstein, et al., "How Common Are Renal Angiomyolipomas in Patients with Pulmonary Lymphangiomyo-matosis?," *Am. J. Respir. Crit. Care Med.* 152:2138-2143 (1995).
Billiau, et al., "Immunomodulatory Properties of Interferon-γ—An Update," *Ann. N.Y, Acad. Sci.* 856:22-32 (1998).

Bjornsson, et al., "Tuberous Sclerosis-Associated Renal Cell Carcinoma—Clinical, Pathological, and Genetic Features," *Am. J. Pathol.* 149:1201-1208 (1996).
Castillenti, et al., "Angiomyolipoma of the Spermatic Cord: Case Report and Literature Review," *J. Urol.* 142:1308-1309 (1989).
Cavet, et al., "Interferon-γ and Interleukin-6 Gene Polymorphisms Associate with Graft-Versus-Host Disease in HLA-Matched Sibling Bone Marrow Transplantation," *Blood* 98:1594-1600 (2001).
Cirelli, et al., "Interferons—An Overview of Their Pharmacology," *Clin. Immunother .* 5:22-30 (1996).
Cook, et al., "A Cross Sectional Study of Renal Involvement in Tuberous Sclerosis," *J. Med. Genet.* 33:480-484 (1996).
Dabora, et al., "Mutational Analysis in a Cohort of 224 Tuberous Sclerosis Patients Indicates Increased Severity of *TSC2*, Compared with *TSC1*, Disease in Multiple Organs," *Am. J. Hum. Genet.* 68:64-80 (2001).
Ewalt, et al., "Renal Lesion Growth in Children with Tuberous Sclerosis Complex," *J. Urol.* 160:141-145 (1998).
Gallin, et al., "Interferon-γ in the Management of Infectious Diseases," *Annals of Internal Med.* 123:216-224 (1995).
Gomez, "Phenotypes of the Tuberous Sclerosis Complex with a Revision of Diagnostic Criteria," *Ann. N.Y. Acad. Sci.* 615:107 (1991).
Ito, et al., "Angiomyolipoma of the Lung," *Arch. Pathol. Lab. Med.* 122:1023-1025 (1998).
Kwiatkowski, et al., "Tuberous Sclerosis," *Arch. Dermatol.* 130:348-354 (1994).
Maesawa, et al., "Angiomyolipoma Arising in the Colon," *Am. J. Gastroenterol.* 91:1852-1854 (1996).
Mogi, et al., "Retroperitoneal Extrarenal Angiomyolipoma with Early Gastric Carcinoma," *J. Gastroenterol.* 33:86-90 (1998).
Pravica, et al., "A Single Nucleotide Polymorphism in the First Intron of the Human IFN-γ Gene: Absolute Correlation with a Polymorphic CA Microsatellite Marker of High IFN-γ Production," *Human Immunol.* 61:8630866 (2000).
Shimizu, et al., "Intramyocardial Angiomyolipoma," *Am. J. Surg. Pathol.* 18:1164-1169 (1994).
Yaegashi et al., "Uterine Angiomyolipoma: Case Report and Review of the Literature," *Pathol. Intl.* 51:896-901 (2001).
Puccetti, et al., "Role of Low Nuclear Grading of Renal Carcinoma Cells in the Functional Profile of Tumor-Infiltrating T Cells," *Int. J. Cancer* 98:674-681 (2002).

* cited by examiner

*Primary Examiner*—Christine J. Saoud
*Assistant Examiner*—Jegatheesan Seharaseyon
(74) *Attorney, Agent, or Firm*—Law Office of Michael A. Sanzo, LLC

(57) ABSTRACT

The present invention is directed to methods of treating or preventing angiomyolipomas by administering interferon gamma. It also encompasses methods for assessing the risk of a patient developing angiomyolipomas based upon interferon gamma expression.

15 Claims, No Drawings

SEQUENCE LISTING

```
<160> NUMBER OF SEQ ID NOS: 2

<210> SEQ ID NO 1
<211> LENGTH: 27
<212> TYPE: DNA
<213> ORGANISM: Homo sapiens

<400> SEQUENCE: 1
agacattcac aattgatttt attctac                                             27

<210> SEQ ID NO 2
<211> LENGTH: 32
<212> TYPE: DNA
<213> ORGANISM: Homo sapiens

<400> SEQUENCE: 2
gtgtcttcct tcctgtaggg tattattata cg                                       32
```

INTERFERON GAMMA IN THE DETECTION AND TREATMENT OF ANGIOMYOLIPOMAS

CROSS REFERENCE TO RELATED APPLICATIONS

This application claims priority to U.S. provisional application No. 60/393,102, filed on Jul. 3, 2002, which is incorporated in its entirety herein by reference.

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to methods of treating patients for angiomyolipomas by administering interferon gamma or agents that increase endogenous interferon gamma levels. In addition, the invention encompasses methods of assessing the likelihood of a patient developing angiomyolipoma growths by determining whether the interferon gamma levels produced by the patient are abnormally low or if the patient has a genotype characteristic of elevated interferon gamma synthesis. The methods disclosed should be especially useful in patients with tuberous sclerosis or lymphangioleio-myomatosis.

BACKGROUND OF THE INVENTION

A. Angiomyolipomas in Tuberous Sclerosis and Lymphangioleiomyomatosis

Tuberous sclerosis is a rare genetic disease that causes benign tumors to form in a variety of tissues including the brain, kidneys, lungs and skin (U.S. Pat. No. 6,326,483; Gomez, *Ann. N.Y. Acad. Sci.* 615:1–7 (1991); Kwiatkowski, et al., *Arch. Dermatol.* 130:348–354 (1994)). Based upon estimates provided by the National Institutes of Health, tuberous sclerosis affects between 25,000 and 40,000 people in the United States and one to two million people worldwide. It is estimated that about one out of every 6,000 newborns has the disorder.

One of the most common problems associated with tuberous sclerosis is the formation of renal angiomyolipomas, benign growths consisting of blood vessels, fatty tissues and muscle cells ((Bjornsson, et al., *Am. J. Path.* 149:1201–1208 (1996); Cook, et al., *J. Med. Genet.* 33:480–484 (1996)). These occur in between 55 and 80% of people with tuberous sclerosis and also occur sporadically in the general population (Ewalt, et al., *J. Urol.* 160:141–145 (1998); Dabora, et al., *Am. J. Hum. Genet.* 68:64–80 (2001)). Angiomyolipomas may grow large enough to cause pain, kidney failure and bleeding. In some instances, they may cause severe blood loss and a life threatening drop in blood pressure. At present, the only treatments available are surgical removal or embolization.

A high frequency of renal angiomyolipomas has also been reported to occur in lymphangioleiomyomatosis (Bernstein, et al., *Am. J. Respir. Crit. Care Med.* 152:2138–2143 (1995)), a rare disease characterized by an unusual type of muscle cell that invades the tissue of the lungs. Although these cells are not considered cancerous, they grow uncontrollably and may eventually interfere with the delivery of oxygen to the rest of the body.

Although angiomyolipomas outside of the kidney or liver are rare, they have been reported as present in a wide variety of other tissues including: the colon (Maesawa, et al., *Am. J. Gastroenterol.* 91:1852–1854 (1996)); heart (Shimizu, et al., *Am. J. Surg. Pathol.* 18:1164–9 (1994)); lung (Ito, et al., *Arch. Pathol. Lab. Med.* 122:1023–1025 (1998)); ovary (Anderson, et al., *Int. J. Gynecol. Pathol.* 21:69–73 (2002)); retroperitoneum (Mogi, et al., *J. Gastroenterol.* 33:86–90 (1998)); skin (Argenyi, et al., *Am. J. Dermatopathol.* 13:497–502 (1991)); spermatic cord (Castillenti, et al., *J. Urol.* 142:1308–1309 (1989)); and uterus (Yaegashi, et al., *Pathol. Int.* 51:896–901 (2001)).

B. Interferon gamma

Interferons are a family of functionally related proteins synthesized by eukaryotic cells in response to viruses and other stimuli (Cirelli, et al., *Clin. Immunother.* 5:22–30 (1996); Billiau, *Ann. N. Y. Acad. Sci.* 856:22–32 (1998); Galli, et al., *Ann. Intern. Med.* 123:216–224 (1995)). They are classified in three groups ("alpha, beta and gamma") based upon their antigenicity and biological characteristics. Interferon gamma is produced mainly upon mitogenic induction of lymphocytes and has potent phagocyte-activating effects not seen with other interferon preparations. The human form of gamma interferon has been patented (U.S. Pat. No. 4,727,138) and is presently being marketed under the trade name "ACTIMMUNE®" as a treatment for chronic granulomatous disease and malignant osteopetrosis.

SUMMARY OF THE INVENTION

The present invention is based on experiments suggesting that there is an inverse correlation between the amount of interferon gamma made by a patient and their likelihood of developing renal angiomyolipomas. The results observed led to the concept that this cytokine may be used to treat or prevent angiomyolipomas and the conditions which give rise to them, particularly tuberous sclerosis and lymphangioleiomyomatosis. In addition, assays of interferon gamma may be used to identify patients with a heightened risk of angiomyolipoma development.

In its first aspect, the invention is directed to a method of treating or preventing tuberous sclerosis, lymphangioleiomyomatosis and angiomyolipomas (especially renal or liver angiomyolipomas) either occurring as a result of these conditions or separately, by administering an effective amount of human interferon gamma. The term "human interferon gamma" refers to the cytokine presently marketed for the treatment of chronic granulomatous disease and malignant osteopetrosis and which is described in detail in U.S. Pat. No. 4,727,138. The term, as used herein refers, not only to the cytokine itself, but also to all forms of the cytokine that are known in the art to be suitable for the treatment of patients. For example, the term encompasses any pharmaceutically acceptable salt of interferon gamma. An "effective amount" is a dosage at which a positive therapeutic effect is observed, i.e., a dosage at which angiomyolipoma growths shrink or the likelihood of angiomyolipoma development is reduced. An effective dose should be between 0.1 and 5 µg per kg patient body, and most typically between 0.5 and 2.5 µg per kg patient body.

In another aspect, the invention is directed to a method of diagnostically evaluating a person for the likelihood that they have, or will develop, angiomyolipomas. There are two methods for accomplishing this, both of which rely upon the observation that high levels of interferon gamma are associated with a reduced likelihood of development. In the first method, a patient is evaluated to determine whether they have an allele (IFNγ allele 2) associated with high interferon gamma production and, consequently, a low risk of angiomyolipoma formation relative to individuals in which the allele is absent. A preferred method of genotype determination is by the polymerase chain reaction (PCR) procedure described in the Examples section herein. However, other procedures are also compatible with the invention.

In the second method of assessing the risk of angiomyolipoma formation, a biological sample is obtained from a patient and the level of interferon gamma is determined directly, e.g., using a commercially available ELISA assay. A comparison may then be made between the level of interferon gamma in the sample and the level present in one or more similar samples obtained from a matched control population. As used in this context, the term "matched control population" refers to people that are similar with respect to known characteristics affecting angiomyolipoma formation other than the particular characteristic assayed. For example, the level of interferon gamma present in a patient with tuberous sclerosis may be compared to the average amount present in tuberous sclerosis patients in general and, based upon this comparison, the risk of angiomyolipoma formation may be assessed. Non-matched control populations could also be used. For example, a comparison could be made with the level interferon gamma present in people in the general population. The ability to select appropriate control populations for these types of assays is well within the capabilities of one of ordinary skill in the art of clinical assay development. The basic concept underlying the assay is that, the lower the level of interferon gamma present, the higher the risk of angiomyolipoma formation.

If the amount of interferon gamma in the patient's sample is lower than the amount in the control samples, this is an indication that the patient has an increased risk of forming angiomyolipomas relative to the people from which the control samples were derived. A higher amount of interferon gamma is an indication that the patient has less chance of angiomyolipoma formation than the controls. The biological samples used in the assay will preferably be blood, plasma, or serum. However, the invention is also compatible with other samples such as urine or lymph. Immunoassays that may be used are described in U.S. Pat. No. 4,666,865 (see also U.S. Pat. No. 6,218,132) and, as mentioned above, are commercially available.

DETAILED DESCRIPTION OF THE INVENTION

The present invention is based upon the concept of treating a patient for angiomyolipomas and conditions that promote angiomyolipoma formation, i.e., tuberous sclerosis and lymphangioleiomyomatosis, by increasing interferon gamma levels. This may be accomplished by either administering the cytokine itself or by administering an agent that increases the endogenous expression of the cytokine. A second, related, concept is that assays of interferon gamma levels can be used to assess the risk of a patient developing angiomyolipoma growths. Patients at high risk may be monitored and given the cytokine as a preventative. It is expected that these treatment and diagnostic methods will be especially useful in patients with tuberous sclerosis or lymphangioleiomyomatosis.

A. Treatment Methods

The present invention is concerned with methods for treating a patient for, tuberous sclerosis, lymphangioleiomyomatosis and angiomyolipomas in general, or preventing angiomyolipoma growth in susceptible individuals, by administering human interferon gamma. Because of their similarity of action, it is believed that other interferons such as interferon alpha and interferon beta will also be beneficial in treating these patients. The methods should be effective both for renal angiomyolipomas, as well as for growths that occur at other sites.

The full length amino acid sequence for human interferon gamma has been disclosed in the literature and methods for its purification and use have been fully described (U.S. Pat. No. 4,727,138). Cytokine suitable for the present methods may be purified from a natural source, made synthetically, or recombinantly produced using any method described in the art. It may also be purchased commercially as ACTIMMUNE® (InterMune™ Pharmaceuticals, Brisbane, Calif.) and used directly in the formulation provided and at the dosages recommended. The methods are compatible with any pharmaceutically acceptable form of human interferon gamma including pharmaceutically acceptable salts or forms of the cytokine that have been modified to improve activity. Alternatively, agents that increase endogenous levels of interferon gamma may be administered to a patient and should have the same effect as the administration of the cytokine per se.

The total dosage of compound to be administered to a patient should be at least the amount required to reduce the number or size of angiomyolipomas and effectiveness in this regard can be determined using standard clinical imaging methods such as performing ultrasound, CT, or MRI scans. The recommended dosage for ACTIMMUNE is 50 μg/m$^2$ for patients with a body surface area greater than 0.5 m$^2$ (equivalent to 1 million IU/m$^2$) and 1.5 μg/kg for patients with a body surface area less than 0.5 m$^2$. For the treatments approved by the FDA it is recommended that these dosages be administered by subcutaneous injection three times a week (e.g., on Monday, Wednesday and Friday). A similar dosing regimen should generally also be effective in the treatment or prevention of tuberous sclerosis, lymphangioleiomyomatosis and angiomyolipomas in general.

In cases where there is a concern about possible side effects, physicians may begin by administering a relatively small dose of compound and then adjust the dosage upward as it becomes clear that a patient can tolerate the treatment. The final dosage may be provided in the regimen described above, although alternative procedures may also be employed. In this regard, it should be recognized that the recommendations herein are simply guidelines since actual dosages and scheduling will be determined by the attending physician based upon clinical factors unique to each patient. The optimal daily dose will be arrived at using methods well known in the art and will be influenced by factors such as the age of the patient, disease state, side effects and other clinically relevant factors. In some cases, a patient may already be taking medications at the time that treatment is initiated. These medications may be continued during the time that interferon gamma is administered provided that no unacceptable adverse side effects are reported by the patient.

In order to determine the effect of treatment on disease, patients should be evaluated on a regular basis over an extended period of time. It may take several weeks for the full therapeutic effect of a treatment to become apparent. Standard clinical methods may be used for assessing the extent to which an improvement has been achieved by drug administration.

The present invention is not limited to any particular dosage form or route of administration. However, oral administration will generally be undesirable due to the destruction of protein in the stomach. The most preferred route of delivery is by subcutaneous injection. The invention is also compatible with other types of injection, as well as transdermal, sublingual, buccal, or implantable forms of administration. Compounds may be given in a substantially purified form, or as part of a pharmaceutical composition containing one or more excipients. Compositions may also include other active agents for the treatment of patients.

The active compound, or compounds, may be incorporated into dosage forms in conjunction with the vehicles that are commonly employed in pharmaceutical preparations, e.g. talc, gum arabic, lactose, starch, magnesium stearate, cocoa butter, aqueous or non-aqueous solvents, paraffin derivatives, glycols, etc. Methods for preparing appropriate formulations are well-known in the art (see e.g., *Remington's Pharmaceutical Sciences*, 16$^{th}$ ed., A. Oslo ed., Easton, Pa. (1980)). An example of a suitable preparation for subcutaneous injection is provided by ACTIMMUNE®. This is supplied in single dose vials with a solution containing in each 0.5 ml: 100 µg (two million IU) of interferon gamma-1b, formulated in 20 mg mannitol, 0.36 mg sodium succinate, 0.05 mg polysorbate 20 and sterile water for injection.

B. Diagnostic Assays

The invention also encompasses methods for assessing the likelihood that an individual will develop angiomyolipoma growths based upon the extent to which they endogenously synthesize interferon gamma. One way of doing this is to directly measure interferon gamma levels in a biological sample (e.g., blood, serum, plasma, urine lymph etc.) obtained from the individual and then compare the results obtained to samples derived from a control population.

Immunoassays suitable for quantitating human interferon gamma levels in biological samples have been thoroughly described in the literature (see e.g., U.S. Pat. Nos. 4,666,865; 6,218,132) and kits are available from many different commercial manufacturers that can be used for samples such as blood, or serum. Manufacturers include: Assay Designs, Inc., Ann Arbor, Mich.; Research Diagnostics, Inc., Flanders, N.J.; eBioscience, Inc, San Diego Calif.; and Hölzel Diagnostika GMBH, Köln, Germany. Any of these assays are suitable for use in the present methods.

Ideally, the control samples should be from people that are similar to the individual being tested with respect to all characteristics likely to distort results. For example, the level of interferon gamma present in a patient with tuberous sclerosis might be compared to the average level present in tuberous sclerosis patients in general. However, other control groups could also be used. For example, a comparison could be made with samples from normal, i.e., disease free, individuals, or tuberous sclerosis patients known to have developed angiomyolipomas. The lower the level of interferon gamma present in the tested individual, the greater the likelihood of their developing angiomyolipoma growths.

As an alternative to directly assaying interferon gamma levels in a patient, they can be tested to determine if they carry a particular allele, IFN-γ allele 2, that has been associated with the production of relatively large amounts of interferon gamma and, as a result, with a reduced likelihood of developing angiomyolipomas. The preferred method for determining whether the patient carries IFN-γ allele 2 is by PCR employing the primers and procedures described detail in the Examples section below. However other procedures for genotyping a person with respect to the IFN-γ gene may also be used.

EXAMPLES

In the present example, we investigate the impact of a non-TSC gene on the renal phenotype in TSC patients in a cohort of 172 patients with known TSC2 mutations. Patients were genotyped for a specific interferon-γ (IFN-γ) microsatellite polymorphism within intron 1 for which one common allele (allele 2 with 12 CA repeats) has been shown to have a higher expression of IFN-γ. Chi square analysis was used to examine the association between IFN-γ allele 2 and the development of kidney angiomyolipomas (KAML) in this TSC2 cohort. Because of the age dependent development of KAML in TSC, we initially focused on the 127 patients over 5 years of age. Additional subgroup analyses were done to investigate the influence of age and gender. The transmission/disequilibrium test (TDT) was also performed in a subset of this cohort (46 probands) in which parent and/or sibling samples were available for analysis.

Both Chi square analysis and TDT suggest there is an association of allele 2 of IFN-γ with the absence of KAML in TSC2 patients. In the 127 patients over 5 years old, KAML was present in 95 (75%) and absent in 32 (25%). In the group with KAML present, the frequency of IFN-γ allele 2 was 56%. In the KAML absent group, the frequency of IFN-γ allele 2 was significantly higher at 78% (p=0.02, Chi square). The family based TDT analysis gave similar results with a TDT statistic ($\chi^2$)=4.89 corresponding to a p value of <0.03. Subgroup analyses show that both age and gender may influence the impact of this association. This study demonstrates that modifying genes play a role in the variable expression in TSC and also suggests a potential medical treatment for KAML in TSC patients.

A. Background

Human IFN-γ is a homodimeric 34 kD peptide secreted by T lymphocytes and natural killer cells. It plays an important role in the coordinated regulation of expression of the immune response via the stimulation or repression of key genes. Human IFN-γ is encoded by a single gene mapped to chromosome 12q24.1 and contains four exons with three introns. The first intron contains a CA microsatellite repeat, which is highly polymorphic with up to 6 alleles. One particular allele (allele 2 with 12 CA repeats) has been shown to be associated with high levels of IFN-γ production in vitro (Pravica, et al., *Eur. J. Immunogenet.* 26:1–3 (1999)), which may be due to its association with a nearby SNP within a putative NF-kappa B binding site (Pravica, et al., *Hum. Immunol.* 61:863–6 (2000)). This allele has been associated with higher or lower risk of a variety of diseases, including rheumatoid arthritis, allograft fibrosis in lung transplant patients, and risk of acute graft vs. host disease in bone marrow transplant patients (Awad, et al., *Hum. Immunol* 60):343–6 (1999); Khani-Hanjani, et al. *Lancet* 356: 820–5 (2000); Cavet, et al., *Blood* 98:1594–1600. (2001)).

Because IFN-γ has been shown to be a useful mediator of tumor regression in animal models of kidney tumors (Lee, et al., *J. Immunol.* 164:231–9 (2000); Becker, et al., *Nat. Med.* 7:1159–62. (2001)), and there is a known high expressing allele of IFN-γ in humans, we examined the relationship between IFN-γ genotype with the severity of renal disease in TSC patients with known TSC2 mutations.

B. Materials and Methods

Patients and TSC Mutation Analysis

172 TSC patients were studied in whom mutations were identified in TSC2 and for whom data on renal phenotype was available. One hundred twenty-one of these patients were previously described (Dabora, et al., *Am. J. Hum Genet* 68:64–80 (2001)) and 51 were new mutations found by similar methods. The presence or absence of KAML was determined by ultrasound or CT imaging. Most (150) patients were referred by pediatric neurology practices (80 from Warsaw, 49 from Cincinnati, 21 from Boston), and the remainder came from mail requests. We included all available patients with both a known pathogenic TSC2 mutation, and clinical information on the presence or absence of KAML.

Interferon-γ Genotyping

Genotyping for the intron 1 CA repeat of the IFN-γ gene was performed by modifying the fluorescent PCR method described by Khani-Hanajani, et al., (*Lancet* 356:820–5 (2000)). The following primers were used: Forward 5'-6-FAM-AGACATTCACAATTGATTTTAT TCTAC (SEQ ID NO:1) and reverse 5'-GTGTCTTCCTTCCTGTAGGGTAT-TATTATACG (SEQ ID NO:2). The underlined portion of the reverse primer is a 7 base-pair clamp that was added to reduce stutter artifact. PCR was performed using AmplitaqR Gold (Perkin Elmer). 20 µl reactions were used with 10 to 50 ng genomic DNA, 0.5 µM of each primer, 10 mM of dNTPs, 0.2 µl of AmplitaqR gold (1U) and the manufacturer's recommended buffers. PCR cycling was carried out on a MJ Research PTC-100 thermal cycler using 95°×12 min, followed by 35 cycles of 94°×30s, 57°×30s for annealing, 72°×45s for extension, and a final extension step at 72°×4 min. The 6-FAM labeled PCR products were run on an ABI 3100 capillary sequencer with HD 400 as a size standard. Genescan 3.7 software (ABI) was used to determine the size of the amplicons to assign the IFN-γ alleles present in each sample.

Statistical Analysis

Chi square, Fisher and t-test analyses were done using Statview 5.0 software. The Chi-square or Fisher was used for nominal variables and one-tailed t-test for quantitative variables. The TDT statistic was calculated:

$$X^2=(b-c)2/(b+c)$$

where X2 is used to calculate the p value from a Chi Square table with 1 degree of freedom, b represents the number of times that the allele of interest is transmitted and c represents the number of times it is non-transmitted.

C. Results

IFN-γ Allele 2 is Associated with Absence of KAML in TSC2 Patients Over 5 Years Old 172 patients with known TSC2 mutations and clinical data on the presence or absence of KAML to investigate the association of IFN-γ allele 2 with the development of KAML in TSC2 patients. Because of the age dependent development of KAML in TSC, we initially considered only the 127 individuals over the age of 5 years. Mutation analysis was performed as described in Dabora et al., 2001 and KAML were detected by renal ultrasound or CT scan. As shown in Table 1, there were 95 (75%) TSC2 patients with KAML present and 32 (25%) with KAML absent in this cohort. Gender and age distribution were similar in both the KAML present and the KAML absent groups. However, the frequency of IFN-γ allele 2 was 25/32 (75%) in the KAML absent group and 53/95 (56%) in the KAML present group. This difference is statistically significant (Chi square analysis, p=0.02). Viewed from an allelic risk perspective, 68% of TSC2 patients with allele 2 have KAML and 32% do not. In contrast, 86% of TSC2 patients without allele 2 have KAML; 14% do not. Thus, TSC2 patients with allele 2 of IFN-γ are approximately twice as likely to be free of KAML as TSC2 patients without IFN-γ allele 2 (see Table 2).

IFN-γ Allele and Genotype Frequencies

The allele and genotype frequencies in this study are shown in Table 3 with comparison to frequencies reported in the literature (Perrey, et al., *Transpl. Immunol.* 6:193–7 (1998)). Although up to six alleles for the CA repeat within intron 1 of IFN-γ have been reported, there are two common alleles (2 and 3) which account for 85–95% of alleles in several studies. In our cohort of 127 patients, alleles 2 and 3 account for 88%. Although the frequencies of alleles in our entire cohort are similar to other studies, there was a lower frequency of allele 2 in the KAML present group (36%) when compared to the KAML absent group (50%). The results were more striking when genotype frequencies were compared (Table 3, bottom). In control cohorts previously published, the frequency of a genotype containing at least one allele 2 is 75%. We found that although the frequency of a genotype containing allele 2 in our entire cohort was fairly close to this at 61.4%, there was a difference in this frequency when the KAML present group was compared with the KAML absent group with a significantly lower frequency of allele 2 in the KAML present group (56% vs. 78%, p=0.02) as stated above.

Similar Spectrum of TSC2 Mutation Types Across Subgroups

We also considered the possibility that the type of TSC2 mutation might influence the development of KAML. As shown in Table 4, although there is some variation in the frequency of mutation type in the KAML present vs. the KAML absent groups, this was not dramatic. Moreover, considering the frequency of all mutations predicted to cause premature truncation (splice, nonsense, frame shift insertions or deletions, larger rearrangements) versus those predicted to change one or a few amino acids (missense and in frame insertions or deletions), there is no difference in the KAML present vs. KAML absent groups (Table 4, bottom).

Age Dependence of IFN-γ Allele 2 and KAML Association

To investigate the possibility that age influences the association of IFN-γ allele 2 with absence of KAML in TSC2, we did additional subset analyses on different age groups in our cohort (see Table 5). We divided our cohort into three age groups (1–5 years, 6–20 years and 21–49 years). When data in these age groups is analyzed, we observed that the association between IFN-γ allele 2 and absence of KAML is present in the 6–20 year old group (p=0.02, Chi square) but not in the others. Because we see evidence of association in the larger 6–49 year group, our age subgroup analysis shows that in the 27 patients from 21–49 years, there is a similar frequency of allele 2 in both the KAML present and KAML absent groups. There is also a puzzling result in the 1–5 year group. Although this group has an expected low rate of KAML (27%) and a lower frequency of allele 2 (61%) in the KAML absent group when compared to the 6–49 yr KAML absent group (allele 2 frequency 78%), there is an unexpectedly high frequency of allele 2 in the 1–5 yr group with KAML present (92%). This inconsistent result is further addressed in the discussion. If we exclude the 1–5 year olds, our data suggests that the association between IFN-γ allele 2 and absence of KAML is strongest in ages 6–20 years.

Association of IFN-γ Allele 2 and Absence of KAML Stronger in Males than in Females We also considered the possibility that gender could be an important variable in the association between IFN-γ allele 2 and absence of KAML. Here we focus on the 6–49 year group and the 6–20 year group. As shown in Table 5, the ratio of females to males in these age groups is close to 50% and the frequency of KAML in both males and females is similar (approximately 75%). In Table 6, we show that there is a similar frequency of IFN-γ allele 2 in the KAML present group. However, in the KAML absent group, the frequency of IFN-γ allele 2 is higher in males than in females. This data suggests the association of IFN-γ allele 2 with absence of KAML is stronger in males than females.

Transmission/Disequilibrium Test Suggests IFN-allele 2 Associated with Reduced Frequency of KAML We also applied the transmission/disequilibrium test (TDT) to this set of patients to confirm the association of allele 2 of IFN-γ with absence of KAML. In this analysis, we included a subset of the same 127 patients (ages 6–49 years) in whom parental DNA samples were available for IFN-γ genotyping. Of the 95 patients with KAML, 111/190 (58%) of their parents were genotyped for the IFN-γ polymorphism, yielding information on transmission or non-transmission of allele 2 in 35 patients (37%). Of the 32 cases with no KAML, 22/64 (34%) of their parents were genotyped, yielding information on transmission in 11 patients (34%). Table 7 summarizes the TDT data. The data at the top of the table includes all informative cases and shows that in the TSC2 patients with KAML present, allele 2 was transmitted in 17 (40%) cases and not-transmitted in another 26 (60%) cases (X2=1.88, p=0.15). We also find that in the case of TSC2 patients with KAML absent, allele 2 was transmitted in 12 (75%) cases and not transmitted in 4 (25%) cases ($\chi^2$=4.0, p<0.05). If we combine the data from the KAML present group with the KAML absent group in these TSC2 patients, we can calculate a more significant combined $\chi^2$ value. As shown in Table 7, the combined $\chi^2$ value increases to 4.90 with a more significant p value of <0.03. Because several investigators have described certain biases in the TDT if incomplete data is included, we have repeated the TDT calculation excluding single parent cases that may introduce bias. This is shown at the bottom of Table 7 and results in a TDT statistic of 5.45 (p<0.025). Although this is a small study it agrees with the Chi square analysis supporting our conclusion that there is an association between IFN-γ allele 2 and absence of KAML development in TSC2 patients.

TABLE 1

IFN-γ allele frequencies in RSC2 patients >5 years old

| | All | KAML absent | KAML present | p value |
|---|---|---|---|---|
| N | 127 | 32 (25%) | 95 (75%) | |
| Male | 58 (46%) | 15 (47%) | 43 (45%) | |
| Female | 69 (54%) | 17 (53%) | 52 (55%) | |
| Mean age (yrs) | 15.2 | 14.1 | 15.6 | 0.37 (NS) |
| Age range | 6–49 years | 6–34 years | 6–49 years | (t test) |
| # allele 2 present (female/male) | 78 (40/38) | 25 (12/13) | 53 (28/25) | 0.02 |
| # allele 2 absent (female/male) | 49 (29/20) | 7 (5/2) | 42 (24/18) | (Chi Sq) |
| % Allele 2 present | 61% | 78% | 56% | |
| % Allele 2 absent | 39% | 22% | 44% | |

TABLE 2

Frequency of KAML in the presence or absence of IFN-γ allele 2 in TSC2 patients >5 years old

| IFN-γ genotype | 2, 2 or X | | X, X | |
|---|---|---|---|---|
| KAML present | 53 | 68% | 42 | 86% |
| | 25 | 32% | 7 | 14% |
| total | 78 | | 49 | |

Allele X represents any allele other than 2.

TABLE 3

IFN-γ allele and genotype frequencies in TSC patients >5 years old

| | KAML absent (n = 32) | KAML present (n = 95) | Entire Cohort (n = 127) | Perrey et al., 1998* (n = 164) |
|---|---|---|---|---|
| Allele | | | | |
| 2 | 50% | 36.3% | 39.8% | 48.2% |
| 3 | 42.2% | 50.5% | 48.4% | 42.7% |
| 4 | 6.3% | 6.8% | 6.7% | 4.3% |
| 5 | 1.6% | 5.8% | 4.7% | 4.9% |
| 6 | 0.0% | 0.5% | 0.4% | 0.0% |
| Genotype | | | | |
| 2, 2 | 21.9% | 16.8% | 18.1% | 20.7% |
| 2, 3 | 46.9% | 29.5% | 33.9% | 47.0% |
| 2, 4 | 6.3% | 5.3% | 5.5% | 3.0% |
| 2, 5 | 3.1% | 4.2% | 3.9% | 4.3% |
| 3, 3 | 15.6% | 27.4% | 24.4% | 14.6% |
| 3, 4 | 0.0% | 8.4% | 6.3% | 4.3% |
| 3, 5 | 3.1% | 7.4% | 6.3% | 5.5% |
| 3, 6 | 1.1% | 1.1% | 0.8% | 0.0% |
| 4, 4 | 0.0% | 0.0% | 0.8% | 0.6% |
| 2, 2 or X8** | 78.1% | 55.8% | 61.4% | 75.0% |
| X, X | 21.9% | 44.2% | 38.6% | 25.0% |

*Perrey, et al., Transpl. Immunol: 6(3): 193–7 (1998).
**Allele X represents any allele other than 2

TABLE 4

TSC2 mutation spectrum in KAML and IFN-γ allele subgroups in TSC Patients >5 years old

| | KAML Present | | KAML Absent | |
|---|---|---|---|---|
| In frame deletion | 7 | 7% | 2 | 6% |
| In frame insertion | 2 | 2% | | 0% |
| missense | 16 | 17% | 6 | 19% |
| Frameshift deletion | 8 | 8% | 7 | 22% |
| Frameshift insertion | 9 | 9% | 2 | 6% |
| nonsense | 29 | 31% | 3 | 9% |
| splice | 17 | 18% | 7 | 22% |
| Large deletion | 7 | 7% | 3 | 9% |
| Duplication | | | 2 | 6% |
| total | 95 | 100% | 32 | 100% |
| In frame deletion or insertion, missense | 25 | 26% | 8 | 25% |
| Nonsense, splice, frameshift or large deletion/duplication | 70 | 74% | 24 | 75% |

TABLE 5

Distribution of KAML, gender, and allele 2 in different age groups of TSC2 patients

| ages | total N | % female total | % KAML + total | % KAML + females | % KAML + males | KAML – group, allele 2 status N | KAML – group, allele 2 status % allele 2 | KAML – group, allele 2 status N | KAML – group, allele 2 status % allele 2 | P value* Chi |
|---|---|---|---|---|---|---|---|---|---|---|
| 1–5 yr | 45 | 42% | 27% | 26% | 27% | 33 | 61% | 12 | 92% | 0.05 |
| 6–20 yr | 100 | 53% | 75% | 75% | 74% | 25 | 84% | 75 | 56% | 0.02 |
| 21–49 yr | 27 | 63% | 74% | 76% | 70% | 7 | 57% | 20 | 55% | 0.30 |
| 6–49 yr | 127 | 55% | 75% | 76% | 74% | 32 | 78% | 95 | 56% | 0.02 |

*No AML vs. Yes

TABLE 6

IFN-γ allele 2 frequencies in males and females

| ages | gender | KAML + group, allele 2 status N | KAML + group, allele 2 status % allele 2 | KAML + group, allele 2 status N | KAML + group, allele 2 status % allele 2 | KAML + vs. – FISHER P value |
|---|---|---|---|---|---|---|
| 6–49 yr | all | 32 | 78% | 95 | 56% | 0.02 |
| 6–49 yr | males | 15 | 87% | 42 | 57% | 0.06 |
| 6–49 yr | females | 17 | 71% | 53 | 55% | 0.28 |
| 6–20 yr | all | 25 | 84% | 75 | 56% | 0.02 |
| 6–20 yr | males | 12 | 100% | 35 | 57% | 0.006 |
| 6–20 yr | females | 13 | 69% | 40 | 55% | 0.52 |

TABLE 7

TDT for allele 2 of IFN-γ and Kidney AML in TSC2 disease

| | IFN-γ allele 2 Transmitted | IFN-γ allele 2 Not Transmitted | Proband # | TDT statistic ($\chi^2$) | P value |
|---|---|---|---|---|---|
| TSC2 and KAML present* | | | | | |
| Observed | 17 (40%) | 26 (60%) | 35 | 1.88 | ~0.15 |
| Expected | 21.5 (50%) | 21.5 (50%) | | | |
| TSC2 and KAML absent* | | | | | |
| Observed | 12 (75%) | 4 (25%) | 11 | 4.0 | <0.05 |
| Expected | 8 (50%) | 8 (50%) | | | |
| Combined* | | | | | |
| Affected (KAML present) | 17 (40%) | 26 (60%) | 35 | 4.90 | <0.03 |
| Not Affected (KAML absent) | 12 (75%) | 4 (25%) | 11 | | |
| Combined** | | | | | |
| Affected (KAML present) | 14 (38%) | 23 (62%) | 30 | 5.45 | <0.025 |
| Not Affected (KAML absent) | 12 (75%) | 4 (25%) | 11 | | |

*all informative cases included
**one parent case with potential bias excluded

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A method of treating a patient for tuberous sclerosis comprising administering to said patient an effective amount of human interferon-gamma or an agent that increases endogenous interferon gamma levels.

2. The method of claim 1, wherein said patient is administered human interferon-gamma.

3. The method of claim 2, wherein said interferon gamma is administered by subcutaneous injection at a dosage of between 0.1 µg/kg body weight and 5 µg/kg body weight.

4. The method of claim 3, wherein said injection is at a dosage of between 0.5 µg/kg body weight and 2.5 µg/kg body weight.

5. The method of either claim 1 or claim 2, wherein said patient is treated for an angiomyolipoma occurring in the kidney.

6. A method of treating a patient for lymphangioleiomyomatosis, comprising administering to said patient an effective amount of human interferon-gamma or an agent that increases endogenous interferon-gamma levels.

7. The method of claim 6, wherein said patient is administered human interferon gamma.

8. The method of either claim 6 or claim 7, wherein said patient is treated for an angiomyolipoma occurring in the kidney.

9. The method of claim 7, wherein said interferon gamma is administered by subcutaneous injection at a dosage of between 0.1 µg/kg body weight and 5 µg/kg body weight.

10. The method of claim 9, wherein said injection is at a dosage of between 0.5 µg/kg body weight and 2.5 µg/kg body weight.

11. A method of treating a patient for and angiomyolipoma, comprising administering to said patient an effective amount of a human interferon.

12. The method of claim 11, wherein said patient is administered human interferon gamma.

13. The method of either claim 11 or claim 12, wherein said angiomyolipoma occurs in the kidney.

14. The method of either claim 11 or claim 12, wherein said interferon is administered by subcutaneous injection at a dosage of between 0.1 µg/kg body weight and 5 µg/kg body weight.

15. The method of either claim 11 or claim 12, wherein said injection is at a dosage of between 0.5 µg/kg body weight and 2.5 µg/kg body weight.

* * * * *

UNITED STATES PATENT AND TRADEMARK OFFICE
CERTIFICATE OF CORRECTION

PATENT NO.        : 7,229,614 B2
APPLICATION NO. : 10/609680
DATED             : July 1, 2003
INVENTOR(S)       : Dabora et al.

It is certified that error appears in the above-identified patent and that said Letters Patent is hereby corrected as shown below:

In column 1, lines 13-15, after "Statement of Government Support" should be corrected to specify the source of funding. The corrected paragraph should read as follows:

-- This invention was made with Government support under Grant No. CA086248 awarded by the National Institutes of Health. The U.S. Government therefore has certain rights in the invention. --

Signed and Sealed this

Eighteenth Day of August, 2009

David J. Kappos
*Director of the United States Patent and Trademark Office*